(12) United States Patent
Amplatz et al.

(10) Patent No.: US 6,468,303 B1
(45) Date of Patent: Oct. 22, 2002

(54) RETRIEVABLE SELF EXPANDING SHUNT

(75) Inventors: Kurt Amplatz, St. Paul; Michael Afremov, St. Louis Park, both of MN (US)

(73) Assignee: AGA Medical Corporation, Golden Valley, MN (US)

( * ) Notice: Subject to any disclaimer, the term of this patent is extended or adjusted under 35 U.S.C. 154(b) by 0 days.

(21) Appl. No.: 09/535,590

(22) Filed: Mar. 27, 2000

(51) Int. Cl.$^7$ .................................................. A61F 2/06
(52) U.S. Cl. ......................................................... 623/1.2
(58) Field of Search ............................... 623/1.23, 1.15, 623/1.26, 1.2, 1.18, 1.5, 1.51, 1.53; 606/213, 151, 191–200

(56) References Cited

U.S. PATENT DOCUMENTS

| | | | |
|---|---|---|---|
| 5,067,489 A | 11/1991 | Lind | 128/772 |
| 5,354,309 A | 10/1994 | Schnepp-Pesch et al. | 606/198 |
| 5,466,242 A | 11/1995 | Mori | 606/198 |
| 5,662,711 A | 9/1997 | Douglas | 623/12 |
| 5,725,552 A * | 3/1998 | Kotula et al. | 606/213 |
| 5,741,333 A * | 4/1998 | Frid | 623/1.15 |
| 5,846,261 A * | 12/1998 | Kotula et al. | 606/213 |
| 5,919,224 A | 7/1999 | Thompson et al. | 623/1 |
| 5,941,896 A | 8/1999 | Kerr | 606/200 |
| 6,019,786 A * | 2/2000 | Thompson | 606/191 |
| 6,113,641 A * | 9/2000 | Leroy et al. | 623/75 |
| 6,176,873 B1 * | 1/2001 | Ouchi | 623/1.15 |

* cited by examiner

Primary Examiner—Michael J. Milano
Assistant Examiner—Tan-Uyen T. Ho
(74) Attorney, Agent, or Firm—Thomas J. Nikolai; Nikolai & Mersereau, P.A.

(57) ABSTRACT

A collapsible medical device and associated method for shunting selected organs and vessels, wherein the medical device is shaped from a shape memory metal fabric. The device may be used, for example, to non-surgically create a transjugular intrahepatic portosystemic shunt. The device is preferably made from a continuous tubular metal fabric and includes two outer flanges that reduce device migration and includes a central passageway between the two outer flanges. The metal fabric may be heat treated within a mold in order to substantially set a desired relaxed shape of the device. The medical device includes a fastener for attaching to the end of a guide wire or delivery catheter. The medical device having the desired relaxed shape may be collapsed and delivered through a catheter or the like for deployment in a desired channel or opening in a patient's body and is retrievable after deployment.

25 Claims, 8 Drawing Sheets

RETRIEVABLE SELF EXPANDING SHUNT

FIELD OF THE INVENTION

The present invention relates generally to a device and non-surgical method for percutaneously shunting certain arterial systems, venous systems and internal organs. More particularly, the present invention relates to a low profile shunting device suitable for non-surgical creation of a communication or "shunt" between, for example without limitation, the portal vein and the hepatic vein using catheter techniques introduced through the jugular vein. The device made in accordance with the invention reduces the likelihood of migration of the shunt and is retrievable during the delivery procedure. The device is particularly well suited for delivery through a catheter or the like to a remote location in the patient's intravenous system or in a vessel or organ within the patient's body.

BACKGROUND OF THE INVENTION

A wide variety of shunting devices are used in various medical procedures. Certain intravascular devices, such as catheters and guide wires, may be used to deliver these shunting devices to a specific location within a patient. For example, a catheter may be used to reach a selective coronary artery within the vascular system wherein a shunt is desired. Alternatively, a catheter and/or guidewire may be used to deliver a shunting device to, for example, an interior chamber of the patient's heart. Certain forms of cogenital disease may require a communication between the right atrium and left atrium. If such a communication is nonexistent or inadequate in size, typically, a communication is created by passing a balloon catheter from the left atrium to the right atrium. This procedure may be referred to as a Rashkind procedure or an atrial septostomy. Over time these communications tend to decrease in diameter. Hence, there is a need for a non-migrating shunt suitable for positioning within a communication formed in the atrial septum. Other uses of a shunt may include delivery of the shunting device to another preselected internal region of the patient. At times it may be desirable to retrieve or reposition the device after it has extended out of a distal end of a delivery catheter. Hence, it would be desirable for the shunting device to be self-expanding yet retrievable.

Shunting devices may be required for treating specific abnormal conditions, such as bi-passing vascular occlusions or some other occlusion within an internal passageway. Without any limitation intended, a patient may require a transjugular intrahepatic portosystemic shunt (TIPS) to provide a communication or shunt between the portal vein and the hepatic vein. In order to interconnect the portal vein and hepatic vein an opening must be created in each vein. The shunt between the portal vein and hepatic vein preferably should expand and have an inner diameter greater than the opening created in the veins. It is desirable for the shunting device to firmly lodge in the veins to avoid rotation and loosening from the veins.

Further, it would be advantageous to provide a shunting device that automatically adjusts to the shape and thickness of the defect. Also, the shunting device should have a means for anchoring each end of the shunt to the corresponding portion of the arterial system, venous system or organ. The inventors of the present invention are not aware of a retrievable, self-expanding shunting device suitable for percutaneous delivery for connecting arterial systems, venous systems, and/or organs. Thus, without limitation, there is a need for a non-invasive, self-expanding, retrievable shunting device. The present invention addresses these and other needs that will become apparent to those skilled in the art from a review of the description of the present invention.

SUMMARY OF THE INVENTION

It is accordingly an object of the present invention to provide a reliable, retrievable, low-profile, self-expanding, shunting device, wherein the device is suitable for connecting arterial systems, venous systems, or organs percutaneously. The device of the present invention is preferably formed from a continuous tubular metal fabric and includes two opposing spaced apart "discs", patches, or retention skirts interconnected by a central member. Each "disc" includes a bore extending therethrough and the center member includes a central passage interconnecting the bore of each disc, thereby providing a passageway between an outer surface of one disc to an outer surface of the other disc.

When forming these intravascular devices from a resilient metal fabric a plurality of resilient strands or wires are provided, with the metal fabric being formed by braiding the resilient strands to create a resilient material. This braided fabric is then deformed to generally conform to a molding surface of a molding element and the braided fabric is heat treated in contact with the surface of the molding element at an elevated temperature. The time and temperature of the heat treatment is selected to substantially set the braided fabric in its deformed state. After the heat treatment, the fabric is removed from contact with the molding element and will substantially retain its shape in the deformed state. The braided fabric so treated defines a relaxed state of a medical device which can be stretched or expanded and deployed through a catheter into a channel in a patient's body. Those skilled in the art will appreciate that the cavities of the molds must mirror the desired shape of the device. Additionally, the mold may include cores and/or cams to adequately form the desired shape and passages there through.

Without any limitation intended, one embodiment of the present invention has a specific shape that is particularly well suited for connecting arterial systems, venous systems, or organs. For example, without limitation, one embodiment of the present invention is particularly well suited for creating a transjugular intrahepatic portosystemic shunt. In the preferred embodiment, the device is constructed from a metal fabric having a plurality of woven metal strands. The device has a relaxed low-profile configuration and includes clamps that allow attachment of the device to an end of a delivery device or guide wire (allowing recovery of the device after placement). The device has a proximal end and a distal end, and clamps or means for securing the metal fabric attached to each end. The clamps inhibit unraveling of the metal fabric. The configuration of the preferred embodiment has a relaxed configuration including two enlarged diameter portions and a central portion disposed between the two enlarged diameter portions wherein the central portion includes a passageway extending between an outer surface of each of the two enlarged diameter portions.

In an alternate embodiment of the present invention, a center axis of at least one of the enlarged diameter portions is offset from a center axis of the center portion. Alternatively, the center axis of each of the enlarged diameter portions may be aligned along the same longitudinal axis and/or may be offset from the center axis of the center portion. Further, the separation distance between the two enlarged diameter portions may be less than a separation distance between a portal vein and hepatic vein, for example, thereby ensuring a taught interconnection between the portal vein and the hepatic vein.

Without any limitation intended, the use of the device of the present invention will be described with respects to creating a transjugular intrahepatic portosystemic shunt (TIPS). Those skilled in the art will appreciate that the shunt of the present invention may be useful in several other applications including for example: shunting the aorta and pulmonary artery to increase blood flow which may be required by patient's having cyanotic cogenital heart disease; cyanotic infants may require a patent ductus arteriosus during development; and/or connection of the gall bladder to the bowel for patient's with wide spread inoperable cancer on the common bile. Further, the device of the present invention may be positioned within a septal defect to reduce but not eliminate the shunting between the left and right chambers of the heart. Although this identification of suitable uses of the present invention is not exhaustive, those skilled in the art will appreciate that the device of the present invention is not limited to a particularly specialized use.

In use, a guide catheter is positioned and advanced in a patient's body such that the distal end of the catheter is adjacent a desired treatment site for treating a physiological condition. The medical device of the present invention having a predetermined shape is then stretched and inserted into the lumen of the catheter. The device is urged through the catheter and out the distal end, whereupon, due to its ability to retain the relaxed configuration, it will tend to substantially return to its relaxed state adjacent the treatment site. Once the device is fully deployed, the physician or user may confirm proper deployment through radiographs or other known non-intrusive means of observing the position of the device within the patient. The guide wire or delivery catheter is then released from the clamp and removed.

Hence, the present invention provides a self-expanding, retrievable device suitable for connecting an arterial system a venous system and/or an organ while providing an inward tension between the connecting vessels or tissue. Further, the present invention is particularly well suited for delivery through a catheter or the like to a desired remote location in the patient's body, wherein the device may be subsequently retrieved. Also, the present invention provides a retrievable, self-expanding shunting device having outer anchoring portions and a central passage. These and other features and advantages of the present invention will become readily apparent to those skilled in the art from a review of the following detailed description of the preferred embodiment in conjunction with the accompanying claims and drawings in which like numerals in the several views refer to corresponding parts.

DETAILED DESCRIPTION OF THE PREFERRED EMBODIMENT

Figure 1:
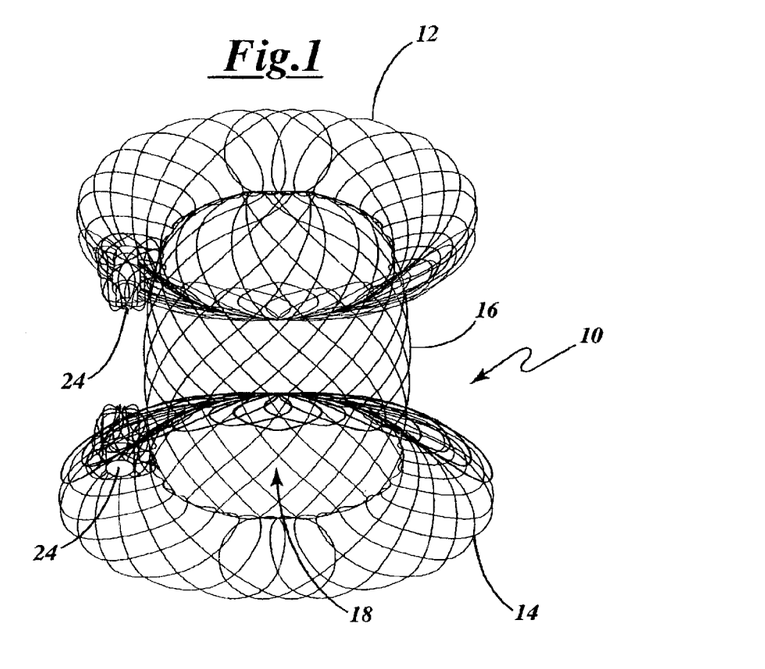
FIG. 1 is a perspective view of a TIPS shunting device in accordance with the present invention.
Figure 2:
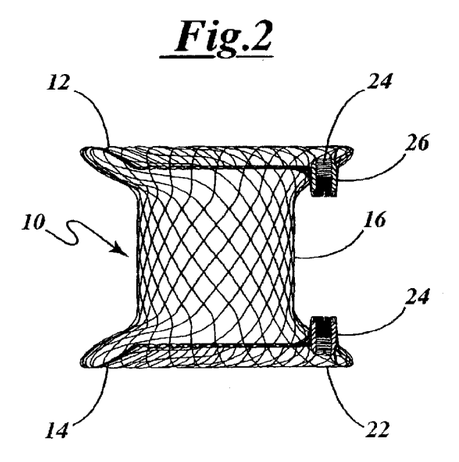
FIG. 2 is a sectional side elevational view of the medical device of the type shown in FIG. 1.
Figure 3:
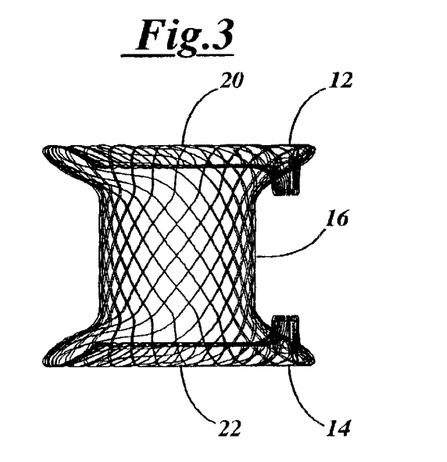
FIG. 3 is a side elevational view of the medical device of the type shown in FIG. 1.

The present invention represents broadly applicable improvements to self-expanding, retrievable shunting devices. The embodiments detailed herein are intended to be taken as representative or exemplary of those in which the improvements of the invention may be incorporated and are not intended to be limiting. Referring first to FIGS. 1–3, the present invention provides a percutaneous catheter directed self-expanding retrievable shunting device 10 that is particularly well suited for use in creating a transjugular intrahepatic portosystemic shunt. The shunting device 10 includes two spaced apart enlarged diameter portions 12 and 14 interconnected by a central portion 16 disposed between the two enlarged diameter portions 12 and 14. The central portion 16 includes a passageway 18 extending between outer surfaces 20 and 22 of respective enlarged diameter portions 12 and 14. The shunting device 10 is preferably made from a tubular metal fabric including a plurality of woven metal strands. A clamp 24 is attached to each outer end of metal fabric, thereby inhibiting unraveling of the metal fabric. At least one of the clamps 24 is adapted for coupling to the end of a guidewire or catheter for delivery to a pre-selected site within the patient.

The tubular "fabric" is formed from a plurality of wire strands having a predetermined relative orientation between the strands. Those skilled in the art will appreciate that the pick and pitch of the braided wires may be varied depending upon the desired density of the fabric. The tubular fabric has metal strands which define two sets of essentially parallel generally spiraling and overlapping strands, with the strands of one set having a "hand", i.e. a direction of rotation, opposite that of the other set. This tubular fabric is known in the fabric industry as a tubular braid.

The pitch of the wire strands (i.e. the angle defined between the turns of the wire and the axis of the braid) and the pick of the fabric (i.e. the number of turns per unit length) as well as some other factors, such as the number of wires employed in a tubular braid, the size or diameter of each wire in the braid, and the diameter of the braid are all important in determining a number of important properties of the device. For example, the greater the pick and pitch of the fabric, and hence the greater the density of the wire strands in the fabric, the stiffer the device will be. Also, the greater the diameter of each wire of the braid, the stiffer the device will be. Having a greater wire density will also provide the device with a greater wire surface area, which will generally enhance the tendency of the device to occlude around the perimeter of the device. This thrombogenicity can be either enhanced by a coating of a thrombolytic agent, or abated by a coating of a lubricious, anti-thrombogenic compound. When using a tubular braid to form a device of the present invention, a tubular braid of about 4 mm in diameter having approximately 72 braided wires is suitable for fabricating devices capable of creating a shunt.

The wire strands of the tubular metal fabric are preferably manufactured from so-called shape memory alloys. A device may be manufactured from a shape memory alloy, wherein the shape of the device may be dependant on temperature or may be manufactured to be independent of temperature. When manufacturing a device from shape memory alloys to be independent of temperature changes, the alloys tend to have a temperature induced phase change which will cause the material to have a preferred configuration which can be fixed by heating the material above a certain transition temperature to induce a change in the phase of the material. When the alloy is cooled back down, the alloy will "remember" the shape it was in during the heat treatment and will tend to assume that configuration independent of temperatures less than the heat treatment temperature, unless constrained from so doing.

Without any limitation intended, suitable wire strand materials may be selected from a group consisting of a cobalt-based low thermal expansion alloy referred to in the field as ELGELOY, nickel-based high temperature high-strength "superalloys" (including nitinol) commercially available from, for example, Haynes International under the trade name HASTELLOY, nickel-based heat treatable alloys sold under the name INCOLOY by International Nickel, and a number of different grades of stainless steel. The important factor in choosing a suitable material for the wire strands is that the wires retain a suitable amount of the deformation induced by a molding surface (as described below) when subjected to a predetermined heat treatment.

In the preferred embodiment, the wire strands are made from a shape memory alloy, NiTi (known as nitinol) which is an approximately stoichiometric alloy of nickel and titanium and may also include other minor amounts of other metals to achieve desired properties. Handling requirements and variations of NiTi alloy composition are known in the art, and therefore such alloys need not be discussed in detail here. U.S. Pat. Nos. 5,067,489 (Lind) and 4,991,602 (Amplatz et al.), the teachings of which are incorporated herein by reference, discuss the use of shape memory NiTi alloys in guide wires. Such NiTi alloys are preferred, at least in part, because they are commercially available and more is known about handling such alloys than other known shape memory alloys. NiTi alloys may also be very elastic and are said to be "super elastic" or "pseudo elastic". This elasticity allows a device of the invention to return to a preset configuration after deployment.

When forming a medical device in accordance with the present invention, an appropriately sized piece of tubular metal fabric is inserted into a mold, whereby the fabric deforms to generally conform to the shape of the cavities within the mold. The shape of the cavities are such that the metal fabric deforms into substantially the shape of the desired medical device. Cores within the cavities may be used to further form the shape of the fabric within the cavities. The ends of the wire strands of the tubular metal fabric should be secured to prevent the metal fabric from unraveling. A clamp 24, welding, or other suitable fastening device may be used to secure the ends of the wire strands. Further, it is to be understood that other suitable fastening means may be attached to the ends in other ways, such as by soldering, brazing, use of biocompatible cementious material or in any other suitable fashion.

During the molding procedure, a molding element may be positioned within the lumen of the tubular braid prior to insertion into the mold to thereby further define the molding surface. If the ends of the tubular metal fabric have already been fixed by a clamp or welding, the molding element may be inserted into the lumen by manually moving the wire strands of the fabric apart and inserting the molding element into the lumen of the tubular fabric. By using such a molding element, the dimensions and shape of the finished medical device can be fairly accurately controlled and ensures that the fabric conforms to the mold cavity.

The molding element may be formed of a material selected to allow the molding element to be destroyed or removed from the interior of the metal fabric. For example, the molding element may be formed of a brittle or friable material. Once the material has been heat treated in contact with the mold cavities and molding element, the molding element can be broken into smaller pieces which can be readily removed from within the metal fabric. If this material is glass, for example, the molding element and the metal fabric can be struck against a hard surface, causing the glass to shatter. The glass shards can then be removed from the enclosure of the metal fabric.

Alternatively, the molding element can be formed of a material that can be chemically dissolved, or otherwise broken down, by a chemical agent which will not substantially adversely affect the properties of the metal wire strands. For example, the molding element can be formed of a temperature resistant plastic resin which is capable of being dissolved with a suitable organic solvent. In this instance, the metal fabric and the molding element can be subjected to a heat treatment to substantially set the shape of the fabric in conformance with the mold cavity and molding element, whereupon the molding element and the metal fabric can be immersed in the solvent. Once the molding element is substantially dissolved, the metal fabric can be removed from the solvent.

Care should be taken to ensure that the materials selected to form the molding element are capable of withstanding the heat treatment without losing its shape, at least until the shape of the fabric has been set. For example, the molding element could be formed of a material having a melting point above the temperature necessary to set the shape of the wire strands, but below the melting point of the metal forming the strands. The molding element and metal fabric could then be heat treated to set the shape of the metal fabric, whereupon the temperature would be increased to substantially completely melt the molding element, thereby removing the molding element from within the metal fabric.

Those skilled in the art will appreciate that the specific shape of the molding element produces a specific shape of the molded device. If a more complex shape is desired, the molding element and mold may have additional parts including a camming arrangement, but if a simpler shape is being formed, the mold may have few parts. The number of parts in a given mold and the shapes of those parts will be dictated almost entirely by the shape of the desired medical device to which the metal fabric will generally conform.

When the tubular braid, for example, is in its preformed relaxed configuration, the wire strands forming the tubular braid will have a first predetermined relative orientation with respect to one another. As the tubular braid is compressed along its axis, the fabric will tend to flare out away from the axis conforming to the shape of the mold. When the fabric is so deformed the relative orientation of the wire strands of the metal fabric will change. When the mold is assembled, the metal fabric will generally conform to the molding surface of the interior cavity. After undergoing the shape memory process, the resulting medical device has a preset relaxed configuration and a collapsed or stretched configuration which allows the device to be passed through a catheter or other similar delivery device. The relaxed configuration is generally defined by the shape of the fabric when it is deformed to generally to conform to the molding surface of the mold.

Once the tubular or planar metal fabric is properly positioned within a preselected mold with the metal fabric generally conforming to the molding surface of the cavities therein, the fabric can be subjected to a heat treatment while it remains in contact with the molding surface. Suitable heat treatment processing of nitinol wire to set a desired shape are well known in the art. Spirally wound nitinol coils, for example, are used in a number of medical devices, such as in forming the coils commonly carried around distal links of guide wires. A wide body of knowledge exists for forming nitinol in such devices, so there is no need to go into great detail here on the parameters of a heat treatment for the nitinol fabric preferred for use in the present invention. Briefly, though, it has been found that holding a nitinol fabric at about 500 degrees centigrade to about 550 degrees centigrade for a period of about 1 to 30 minutes, depending upon the softness or hardness of the device to be made will tend to set the fabric in its deformed state, i.e., wherein it conforms to the molding surface of the mold cavities. At lower temperatures, the heat treatment time will tend to be greater (e.g., about 1 hour at about 350 degrees centigrade) and at higher temperatures the time will tend to be shorter (e.g., about 30 seconds at about 900 degrees centigrade). These parameters can be varied as necessary to accommodate variations in the exact composition of the nitinol, prior heat treatment of the nitinol, the desired properties of the nitinol in the finished article, and other factors known to those skilled in this field.

Instead of relying on convection heating or the like, it is also known in the art to apply an electrical current to the nitinol to heat it. In the present invention, this can be accomplished by, for example, connecting electrodes to each end of the metal fabric. The wire can then be heated by resistance heating of the wires in order to achieve the desired heat treatment, which will tend to eliminate the need to heat the entire mold to the desired heat treating temperature in order to heat the metal fabric to the desired temperature. The materials, molding elements and methods of molding a medical device from a tubular or planar metal fabric is further described in U.S. Pat. No. 5,725,552.

Heat treating the metal fabric at temperatures ranging between 500–550 degrees centigrade substantially sets the shapes of the wire strands in a reoriented relative position conforming the shape of the fabric to the molding surface. When the metal fabric is removed from the mold, the fabric maintains the shape of the molding surfaces of the mold cavities to thereby define a medical device having a desired shape. After the heat treatment, the fabric is removed from contact with the molding cavity and will substantially retain its shape in a deformed state. If a molding element is used, this molding element can be removed as described above.

The time required for the heat treating process will depend in large part upon the material of which the wire strands of the metal fabric are formed and mass of the mold, but the time and temperature of the heat treatment should be selected to substantially set the fabric in its deformed state, i.e., wherein the wire strands are in their reoriented relative configuration and the fabric generally conforms to the molding surface. The required time and temperature of the heat treatment can vary greatly depending upon the material used in forming the wire strands. As noted above, one preferred class of materials for forming the wire strands are shape memory alloys, with nitinol, a nickel titanium alloy, being particularly preferred. If nitinol is used in making the wire strands of the fabric, the wire strands will tend to be very elastic when the metal is in its austenitic phase; this very elastic phase is frequently referred to as a super elastic or pseudo elastic phase. By heating the nitinol above a certain phase transition temperature, the crystal structure of the nitinol metal will tend to "set" the shape of the fabric and the relative configuration of the wire strands in the positions in which they are held during the heat treatment.

Once a device having a preselected shape has been formed, the device may be used to treat a physiological condition of a patient. A medical device suitable for treating the condition is selected. Once the appropriate medical device is selected, a catheter or other suitable delivery device may be positioned within a channel in a patient's body to place the distal end of the delivery device adjacent the desired treatment cite.

The delivery device (not shown) can take any suitable shape, but desirably comprises an elongate flexible metal shaft having a threaded distal end. The delivery device can be used to urge the medical device through the lumen of a catheter for deployment in a patient's body. When the device is deployed out the distal end of the catheter, the device will still be retained by the delivery device. Once the medical device is properly positioned within the patient the metal shaft or guidewire can be rotated about its axis to unscrew the medical device from the threaded distal end of the shaft. The catheter and guidewire are then withdrawn.

By keeping the medical device attached to the delivery means, the operator can retract the device for repositioning, if it is determined that the device is not properly positioned. A threaded clamp attached to the medical device allows the operator to control the manner in which the medical device is deployed out the distal end of the catheter. When the device exits the catheter, it will tend to resiliently return to a preferred relaxed shape. When the device springs back into this shape, it may tend to act against the distal end of the catheter effectively urging itself forward beyond the end of the catheter. This spring action could conceivably result in improper positioning of the device if the location of the device within a channel is critical, such as where it is being positioned as a shunt between two vessels. Since the threaded clamp can enable the operator to maintain a hold on the device during deployment, the spring action of the device can be controlled by the operator to ensure proper positioning during deployment.

Figure 11:
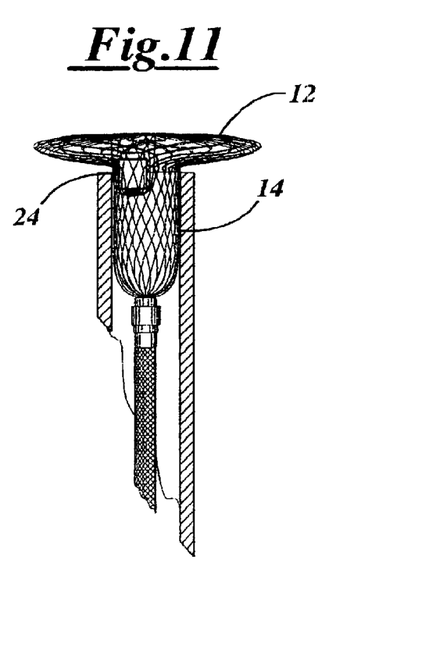
FIG. 11 is a partial sectional side elevational view of the medical device of the type shown in FIG. 1, shown partially extending from a delivery catheter.

The medical device can be collapsed into its collapsed configuration and inserted into the lumen of the catheter. The collapsed configuration of the device may be of any shape suitable for easy passage through the lumen of a catheter and proper deployment out the distal end of the catheter. For example, the TIPS occluding device may have a relatively elongated collapsed configuration wherein the device is stretched along its longitudinal axis (see FIG. 11). This collapsed configuration can be achieved simply by stretching the device generally along its axis, e.g. by manually grasping the clamps and pulling them apart, which will tend to collapse the relaxed diameter portions of the device inwardly toward the device's axis. Loading such a device into a catheter may be done at the time of implantation and does not require pre-loading of the introducer or catheter.

Figure 12:
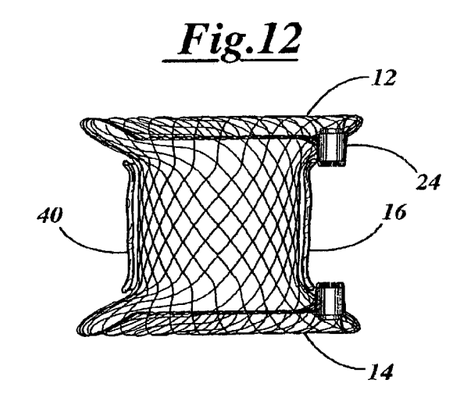
FIG. 12 is a partial sectional side elevational view of an alternate preferred shunting device in accordance with the present invention, having an occluding member extending about the central portion.
Figure 13:
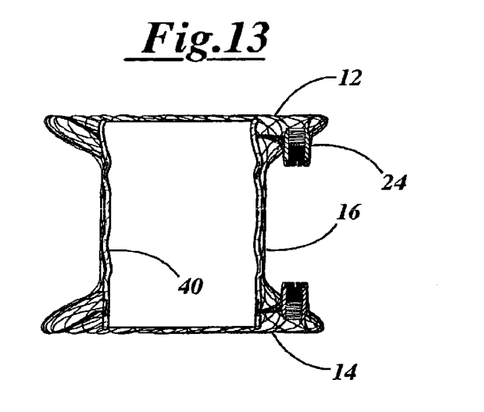
FIG. 13 is a partial sectional side elevational view of an alternate preferred shunting device in accordance with the present invention, having an occluding member engaged to an inner wall of the central portion.
Figure 14:
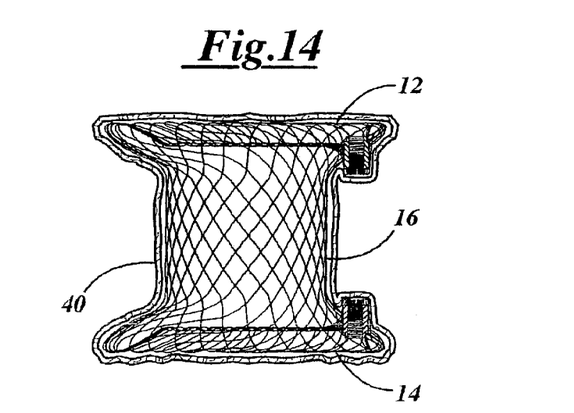
FIG. 14 is a partial sectional side elevational view of an alternate preferred shunting device in accordance with the present invention, having an occluding member engaged to an outer perimeter of the shunting device.
Figure 15:
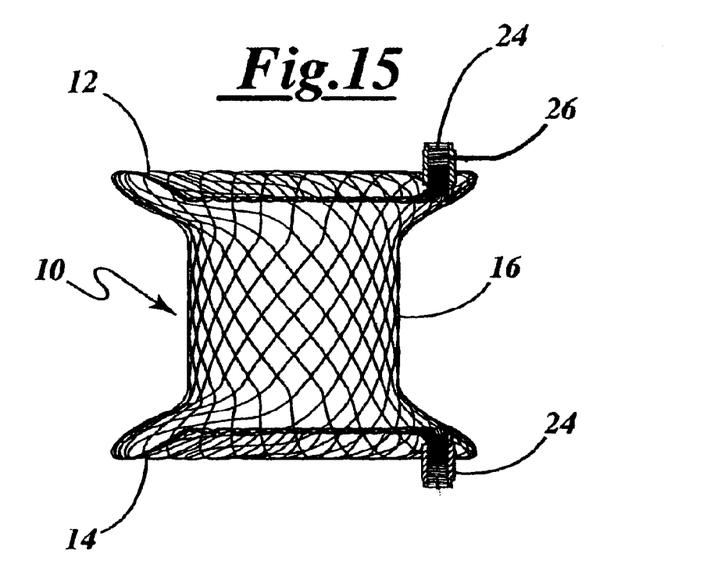
FIG. 15 is a sectional side elevational view of the medical device of the type shown in FIG. 2 having the clamp extending above the planar surface of the enlarged diameter portions.
Figure 16:
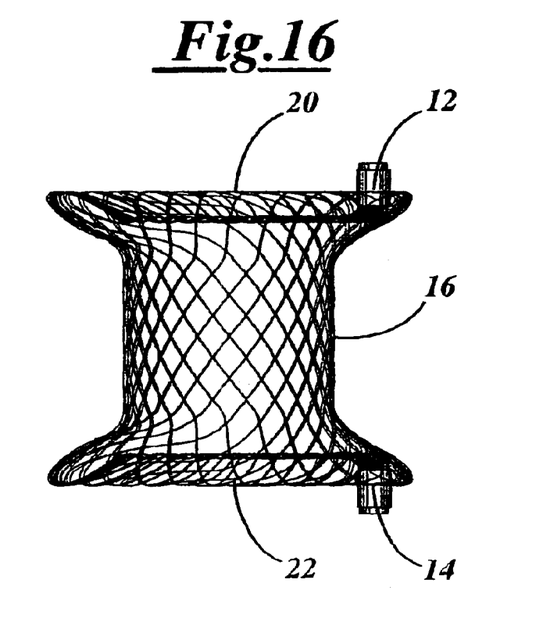
FIG. 16 is a side elevational view of the medical device of the type shown in FIG. 3 having the clamp extending above the planar surface of the enlarged diameter portions.

When the device is deployed in a patient, thrombi will tend to collect on the surface of the wires. By having a greater wire density, the total surface area of the wires will be increased, increasing the thrombotic activity around the perimeter of the device and permitting it to relatively rapidly create a shunt. It is believed that forming the shunting device from a 4 mm diameter tubular braid having a pick of at least about 40 and a pitch of at least about 30 will provide sufficient surface area to efficiently create the shunt. If it is desired to increase the rate at which the perimeter of the device occludes, any of a wide variety of known thrombotic agents can be applied to the device. Those skilled in the art will appreciate that an occluding membrane, fiber, or mesh may be partially or completely wrapped around or within the device to further define the shunt (see FIGS. 12–14).

Figure 9:
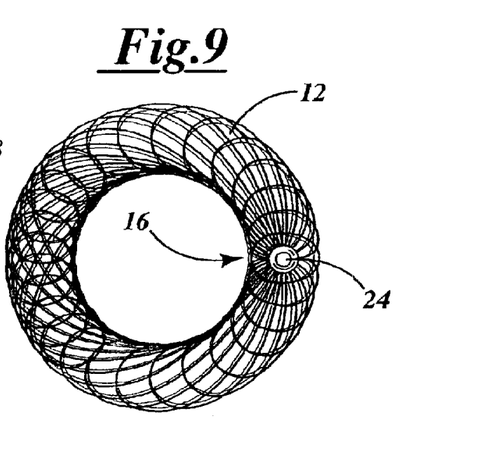
FIG. 9 is a top plan view of the shunting device of the type shown in FIG. 3.
Figure 10:
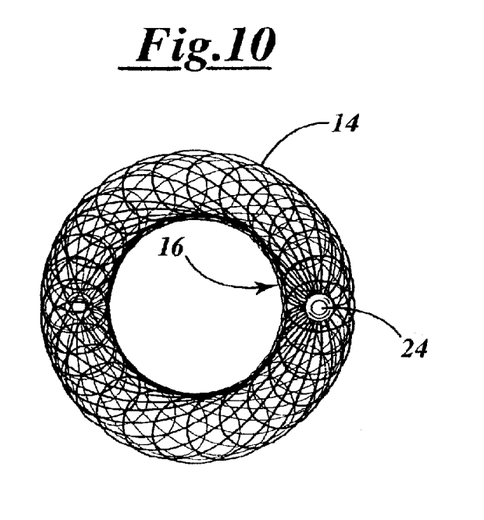
FIG. 10 is a bottom plan view of the shunting device of the type shown in FIG. 3.

The Figures illustrate several embodiments of the shunting device wherein a passageway extends through a central portion of the device. Those skilled in the art will appreciate that the each embodiment may be particularly well suited for a particular medical procedure. Referring to FIGS. 1–3 and 15–16, the shunting device 10 is particularly well suited for creating a TIPS. In its relaxed, unstretched state (see FIGS. 2 and 15), the device 10 generally includes two aligned discs 12 and 14 linked together by a hollow central portion 16. Without any limitation intended, during the formation of the device 10, the tubular braid (in the region forming each enlarged diameter portion 12 and 14) is partially flattened (see also FIGS. 9–11) to reduce the overall size of the device. Those skilled in the art will appreciate that the flattened diameter portions 12 and 14 may be curved inward towards each other to provide a sealing edge.

The clamps 24 tying together the wire strands at corresponding ends serve to connect the device 10 to a delivery system. In the embodiment shown, at least one of the clamps 24 are generally cylindrical in shape and have a threaded bore 26 (see FIG. 2) for receiving the ends of the metal fabric to substantially prevent the wires from moving relative to one another. The threaded bore 26 is adapted to receive and engage a threaded distal end of a delivery device. The clamp 24 may be recessed below the planar surface of the enlarged diameter portions (see FIGS. 2 and 3) or may extend above the surface (see FIGS. 15 and 16). Those skilled in the art will appreciate that the device 10 is sized in proportion to the shunt to be created. Also, the length of the central portion may be varied depending upon the separation distance between the two members to be shunted.

Figure 4:
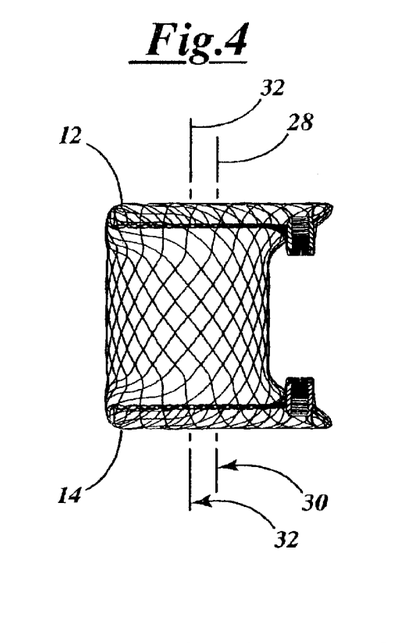
FIG. 4 is a partial sectional side elevational view of an alternate preferred shunting device in accordance with the present invention.
Figure 5:
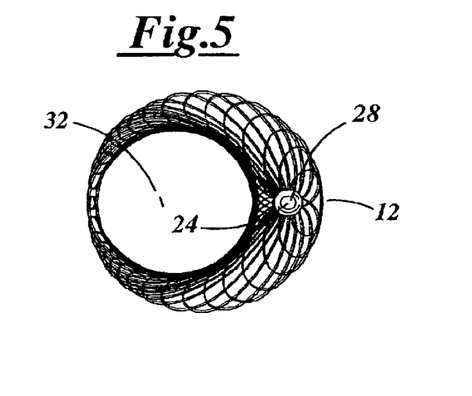
FIG. 5 is a top plan view of the shunting device of the type shown in FIG. 4.
Figure 6:
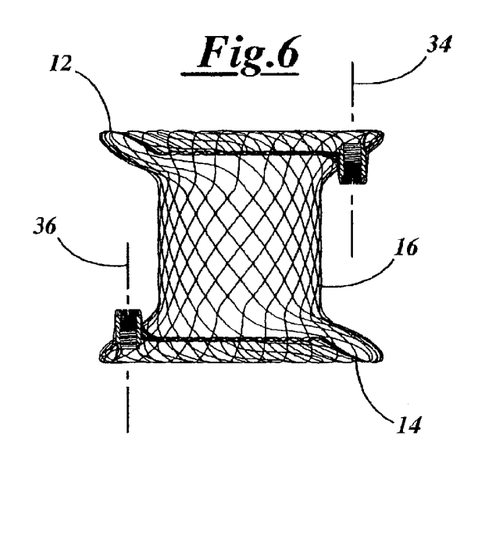
FIG. 6 is a partial sectional side elevational view of an alternate preferred shunting device in accordance with the present invention.
Figure 7:
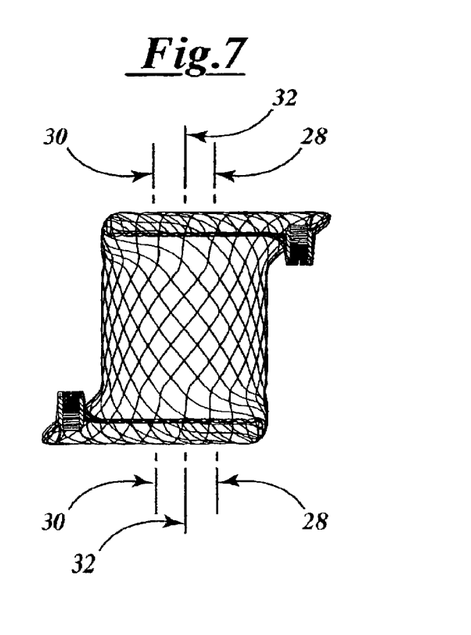
FIG. 7 is a partial sectional side elevational view of an alternate preferred shunting device in accordance with the present invention.
Figure 8:
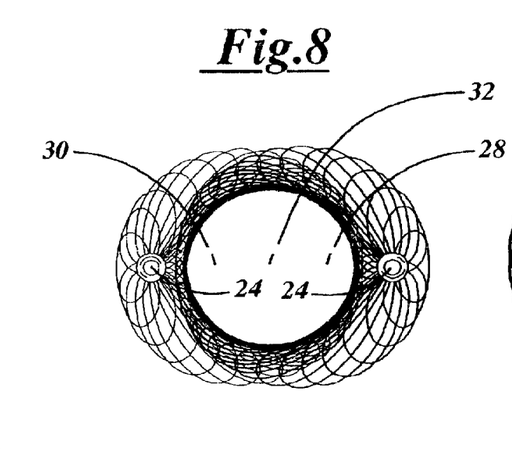
FIG. 8 is a top plan view of the shunting device of the type shown in FIG. 7.
Figure 17:
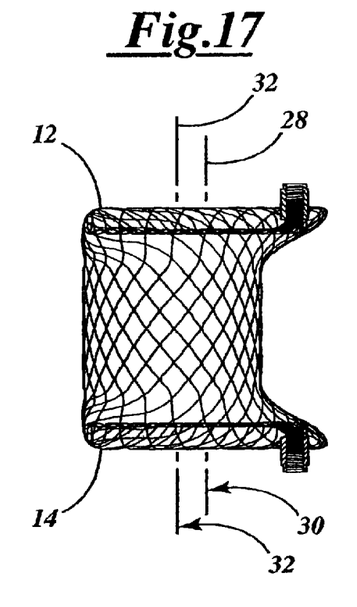
FIG. 17 is a partial sectional side elevational view of the medical device of the type shown in FIG. 4 having the clamp extending above the planar surface of the enlarged diameter portions.
Figure 18:
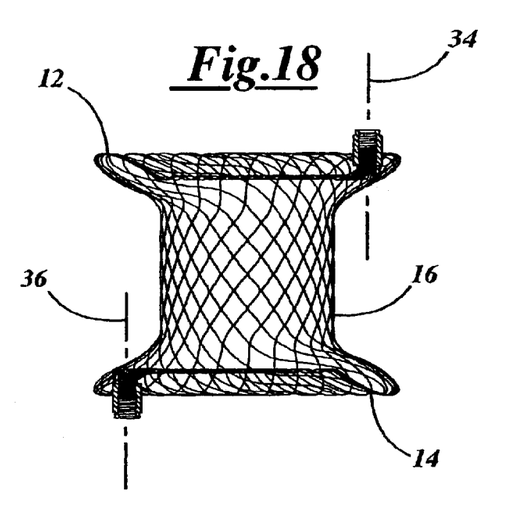
FIG. 18 is a partial sectional side elevational view of the medical device of the type shown in FIG. 6 having the clamp extending above the planar surface of the enlarged diameter portions.
Figure 19:
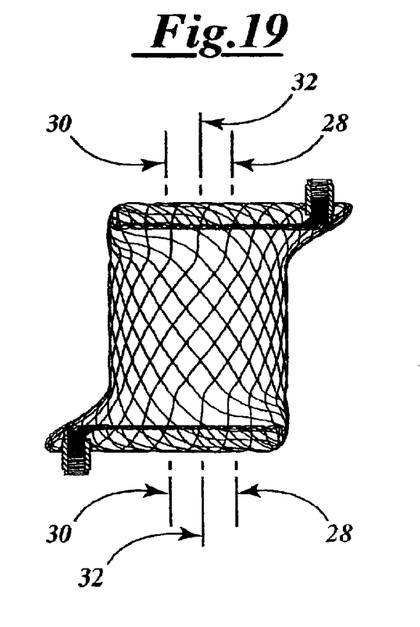
FIG. 19 is a partial sectional side elevational view of the medical device of the type shown in FIG. 7 having the clamp extending above the planar surface of the enlarged diameter portions.
Figure 20:
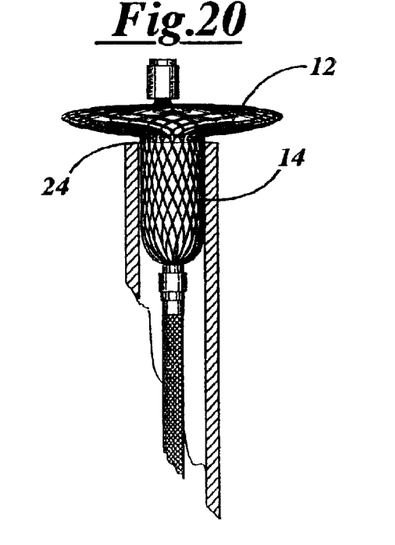
FIG. 20 is a partial sectional side elevational view of the medical device of the type shown in FIG. 15, shown partially extending from a delivery catheter.
Figure 21:
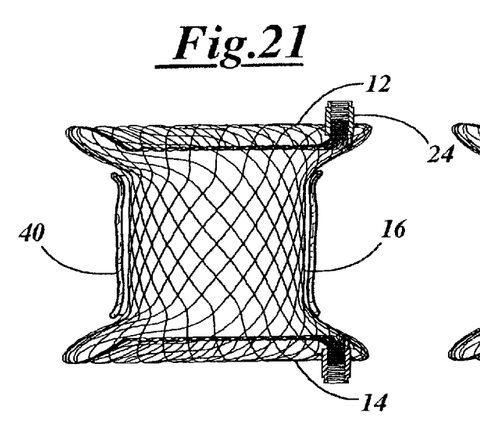
FIG. 21 is a partial sectional side elevational view of the medical device of the type shown in FIG. 12 having the clamp extending above the planar surface of the enlarged diameter portion and having an occluding member extending about the central portion.
Figure 22:
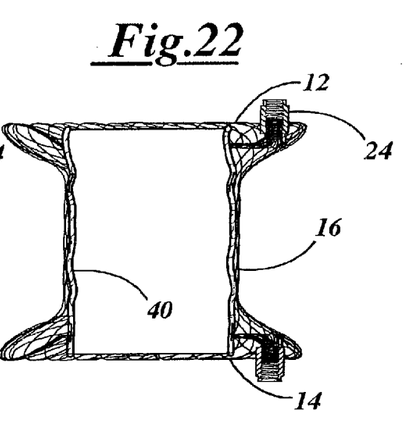
FIG. 22 is a partial sectional side elevational view of the medical device of the type shown in FIG. 13 having the clamp extending above the planar surface of the enlarged diameter portion and having an occluding member engaged to an inner wall of the central portion.
Figure 23:
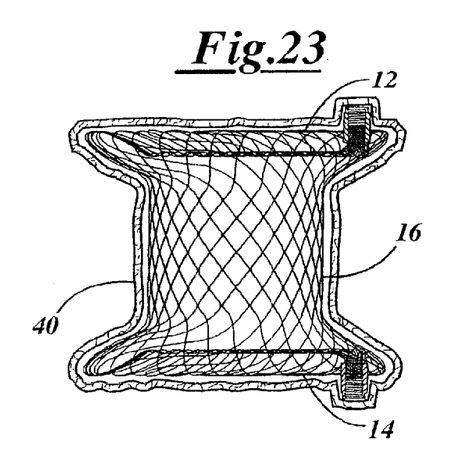
FIG. 23 is a partial sectional side elevational view of the medical device of the type shown in FIG. 14 having the clamp extending above the planar surface of the enlarged diameter portion and having an occluding member engaged to an outer perimeter of the shunting device.
Figure 24:
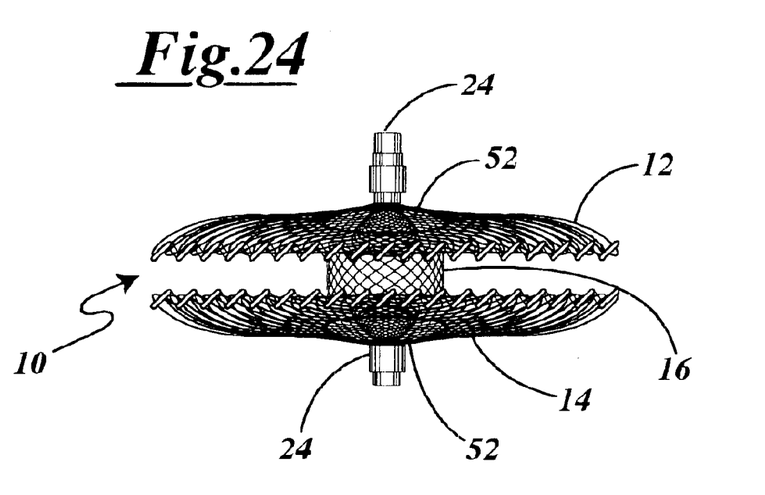
FIG. 24 is a partial sectional side elevational view of another embodiment of the present invention.
Figure 25:
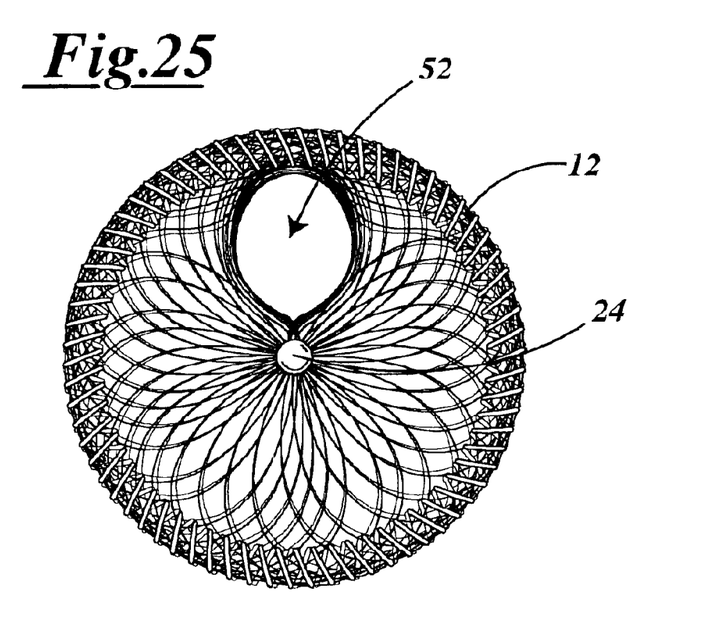
FIG. 25 is a top plan view of the device shown in FIG. 24.

The particular configuration of the shunting device 10 may be modified to meet the particular needs and applications. For example, the embodiment shown in FIGS. 4, 5, and 17 shows the central axis 28 and 30 of each enlarge diameter portion 12 and 14 respectively aligned but offset from the central axis 32 of the central portion 16. FIGS. 6 and 18 show that the central axis 34 and 36 of each clamp 24 need not be aligned in the same plane. FIGS. 7, 8, and 19 show that the central axis 28 and 30 of each enlarged diameter portion 12 and 14 may be offset relative to the other. FIGS. 24 and 25 shows an embodiment of the shunting device 10 of the present invention suitable to shunt a septal defect of a patient's heart. The patient having the septal defect may also suffer from high pulmonary hypertension. For example, it may be desirable to create a shunt in the atrial septum of a neonate with hypoplastic left heart syndrome (HLHS) or with a transposition of the great arteries. In such instances it is desirable to create a shunting passage 52 to allow at least a certain amount of blood to pass between the chambers to accommodate the high pulmonary hypertension. In this manner, mixing of pulmonary and systemic venous blood increases, thereby improving oxygen saturation. Those skilled in the art will appreciate that one or more shunting passages 52 of varying size may be formed in the shunting device 10, to attain the desired amount of shunting. For example, without limitation, the approximate diameter of the shunting passage 52 may be slightly greater than half the diameter of the central portion 16. Depending upon the hemodynamics, one or more of the shunting passages can be closed by an occluding device later on.

Further, as described above, a portion of or all of the outer metal fabric surface or inner metal fabric surface of the shunting device 10 may be enclosed by a biocompatible occluding member 40 (see FIGS. 12–14 and 21–23). Without any limitation intended, the occluding member 40 may comprise a suitable fabric manufactured by Gore, Inc. of Delaware.

This invention has been described herein in considerable detail in order to comply with the Patent Statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A collapsible medical device, comprising a metal fabric including a plurality of woven metal strands having a proximal end and a distal end, each end having means for securing the metal fabric attached thereto, thereby inhibiting unraveling of the metal fabric, the means for securing further including means adapted for attachment to a delivery device, said metal fabric having a relaxed configuration having two enlarged diameter portions and a central portion disposed between the two enlarged diameter portions wherein said central portion includes a passageway for conducting a body fluid extending between and through an outer surface of each of said two enlarged diameter portions, said device further having a collapsed configuration for delivery through a channel in a patient's body.

2. The device according to claim 1, wherein a center axis of at least one of said enlarged diameter portions is offset from a center axis of said center portion.

3. The device according to claim 1, wherein a center axis of a least one of said enlarged diameter portions is aligned with a center axis of said center portion.

4. The device according to claim 1, wherein a center axis of each of said enlarged diameter portions is aligned along the same longitudinal axis.

5. The device according to claim 1, wherein a center axis of each of said enlarged diameter portions is aligned with a center axis of said center portion.

6. The device according to claim 1, wherein a separation distance between the two enlarged diameter portions is less than a separation distance between a portal vein and hepatic vein.

7. The device according to claim 1, wherein said device is formed from a metal fabric consisting of a plurality of woven metal strands.

8. The device according to claim 1, wherein said means for securing is at least partially recessed below the outer surface of said enlarged diameter portion.

9. The device according to claim 1, further including at least two central portions disposed between the two enlarged diameter portions.

10. A collapsible medical device, comprising a metal fabric including a plurality of woven metal strands having a proximal end and a distal end, each end having a securing member attached to the metal fabric, thereby inhibiting unraveling of the metal fabric, the securing member including a threaded bore for attachment to a delivery device, said metal fabric having a relaxed configuration having two enlarged diameter portions and a central portion disposed between the two enlarged diameter portions wherein said central portion includes a passageway for conducting a body fluid extending between and through an outer surface of each of said two enlarged diameter portions, said device further having a collapsed configuration for delivery through a channel in a patient's body.

11. The device according to claim 10, wherein a center axis of at least one of said enlarged diameter portions is offset from a center axis of said center portion.

12. The device according to claim 10, wherein a center axis of a least one of said enlarged diameter portions aligns with a center axis of said center portion.

13. The device according to claim 10, wherein a center axis of each of said enlarged diameter portions is aligned along the same longitudinal axis.

14. The device according to claim 10, wherein a center axis of each of said enlarged diameter portions is aligned with a center axis of said center portion.

15. The device according to claim 10, wherein a separation distance between the two enlarged diameter portions is less than a separation distance between a portal vein and hepatic vein.

16. The device according to claim 10, wherein said means for securing includes means for attachment to a delivery device.

17. The device according to claim 10, wherein said device is formed from a metal fabric consisting of a plurality of woven metal strands.

18. The device according to claim 10, wherein said means for securing is at least partially recessed below the outer surface of said enlarged diameter portion.

19. A collapsible medical device, comprising a metal fabric including a plurality of woven metal strands having a proximal end and a distal end, each end having a securing member attached to the metal fabric, thereby inhibiting unraveling of the metal fabric, at least one of said securing means including means for attachment to a delivery device, said metal fabric having a relaxed configuration having two enlarged diameter portions and a central portion disposed between the two enlarged diameter portions, wherein a separation distance between the two enlarged diameter portions is less than a separation distance between a portal vein and hepatic vein, said central portion includes a passageway for conducting a body fluid extending between and through an outer surface of each of said two enlarged diameter portions, said device further having a collapsed configuration for delivery through a channel in a patient's body.

20. The device according to claim 19, wherein a center axis of at least one of said enlarged diameter portions is offset from a center axis of said center portion.

21. The device according to claim 19, wherein a center axis of a least one of said enlarged diameter portions is aligned with a center axis of said center portion.

22. The device according to claim 19, wherein a center axis of each of said enlarged diameter portions is aligned along the same longitudinal axis.

23. The device according to claim 19, wherein a center axis of each of said enlarged diameter portions is aligned with a center axis of said center portion.

24. The device according to claim 19, wherein said device is formed from a metal fabric consisting of a plurality of woven metal strands.

25. The device according to claim 19, wherein said means for securing is at least partially recessed below the outer surface of said enlarged diameter portion.

* * * * *